United States Patent
Rao et al.

(10) Patent No.: US 6,841,687 B2
(45) Date of Patent: Jan. 11, 2005

(54) PROCESS FOR THE PREPARATION OF (-)-EPICATECHIN FROM A NEW NATURAL SOURCE NAMELY *DICHROSTACHYS CINEREA*

(75) Inventors: Janaswamy Madhusudana Rao, Hyderabad (IN); Rao Jagadeeshwar Rao, Hyderabad (IN); Jhillu Singh Yadav, Hyderabad (IN); Kondapuram Vijaya Raghavan, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/372,641

(22) Filed: Feb. 24, 2003

(65) Prior Publication Data

US 2004/0116717 A1 Jun. 17, 2004

(51) Int. Cl.⁷ ............................................. C07D 311/62
(52) U.S. Cl. ........................................................ 549/399
(58) Field of Search ......................................... 549/399

(56) References Cited

PUBLICATIONS

Krishnamoorthy et al., J. Scientific and industrial Research, Sect. B: Physical Sciences (1962), vol. 21B, pp. 591–593.*

* cited by examiner

*Primary Examiner*—Taofiq Solola
(74) *Attorney, Agent, or Firm*—Ladas & Parry

(57) ABSTRACT

This invention relates to a process for isolating (−)-epicatechin from a new plant source namely *Dichrostachys cinerea* in significant yield.

2 Claims, 1 Drawing Sheet

(-)-Epicatechin

PROCESS FOR THE PREPARATION OF (-)-EPICATECHIN FROM A NEW NATURAL SOURCE NAMELY *DICHROSTACHYS CINEREA*

FIELD OF THE INVENTION

This invention relates to the isolation of a compound namely (-)-epicatechin from a new plant source, *Dichrostachys cinerea* in good yield.

BACKGROUND ART

*Dichrostachys cinerea* is a medicinal plant used in the traditional Indian system of medicine and is widely advocated in diuretic, lithotriptic, anodyne, digestive, constipating, and inflammatory conditions. Also it is useful in vitiated conditions of kapha and vata, arthralgia, elephantiasis, dyspepsia, diarrhea, vesicle calculi, strangury, nephropathy, vaginopathy and metropathy.(*Indian Medicinal Plants*, Vol.2 p.330). It is useful in opthalmia, rheumatism, urinary calculi and renal troubles.(*Wealth of India* Vol.3 p.56). It is further reported to possess protease inhibitor activity(CA, 90, 118086u), fungi toxic activity (*Ind. J. plant. Physiol*, 1986, 29(3), 278–80.), antibacterial (*Fitoterapia*, 1988, 59(1), 57–62.). Hence it becomes pertinent to look for the molecules possessing such important biological properties. In this connection, the phytochemical investigation of *Dichrostachys cinerea* has been taken up. The applicants made efforts for the isolation of a compound (-)-epicatechin in highly economical yield.

OBJECTS OF THE INVENTION

The main object of the invention is to provide a process for preparation of (-)-epicatechin from a new natural source *Dichrostachys cinerea*.

Another object of invention is to provide a new source for obtaining (-)-epicatechin in good yield.

(-)-Epicatechin known to posses several activities, which are shown in Table.1

TABLE 1

| Compound | Activity | Reference |
|---|---|---|
| (-)-Epicatechin | 1. Anti-viral activity | CA 89: 192312k |
| | 2. Anti-diabetic activity | Indian Drugs, 1981, 18(5), 184–5 |
| | 3. Inhibitory effects on lipid peroxidation in mitochondria and microcosms of Liver | Chem. Pharm. Bull, 1983, 31(5), 1625 |
| | 4. Inhibition of angiotension-I-converting enzyme | Planta Med, 1987, 53(1), 12–15 |
| | 5. Inhibition of HIV-1 reverse transcriptase by catechins | Bio Chem. Jour, 1992, 288(3), 717–719 |
| | 6. Antioxidant activity | J.Chem.Soc.perkin trans 2, 1998, 4, 911–15 |

SUMMARY OF THE INVENTION

The present invention relates to a process for the isolation of (-)-epicatechin from *D. cinerea*.

DETAILED DESCRIPTION

Figure 1:
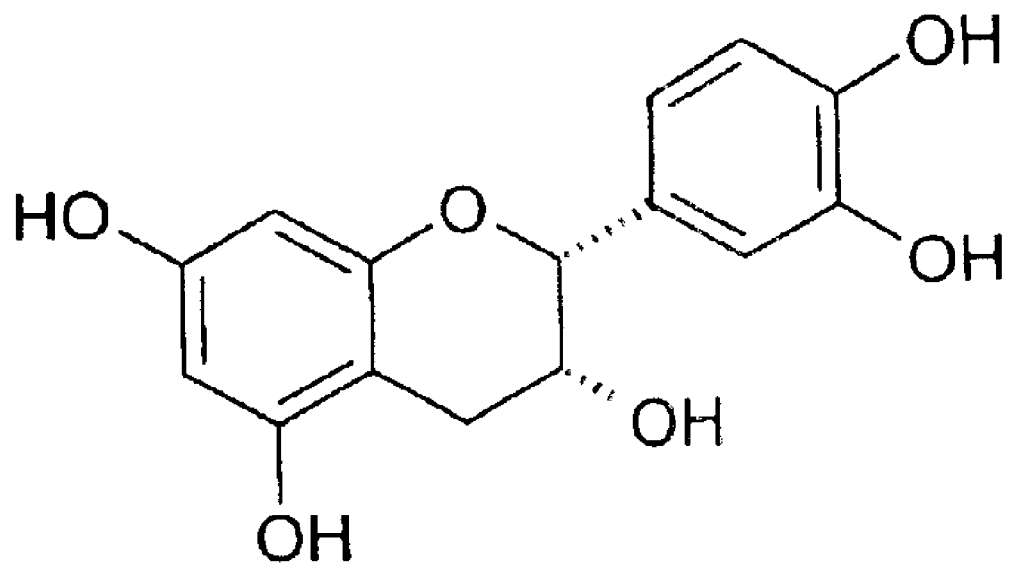
FIG. 1 represents the structure of (-) -epicatechin.

The present invention provides a process for isolation of (-)-epicatechin from *D. cinerea* comprises of the following steps:

(a) extracting dried wood powder of *Dichrostachys cinerea* with hexane;
(b) extracting the residue of step (a) with chloroform;
(c) extracting the residue of step (b) with methanol;
(d) concentrating the methanol solution from step (c) under vacuum;
(e) adsorbing the methanol extract on silica gel (60–120 mesh) and loading on silica gel (60–120 mesh) column (5 cm diameter to height of 100 cm);
(f) eluting the column with chloroform methanol gradient,
(g) collecting the fraction eluted at 6% methanol in chloroform, and
(h) concentrating the eluted fraction to obtain pure (-)-epicatechin.

In another embodiment of the present invention, the solvent used or selected from Hexane, Chloroform and Methanol.

In another embodiment of the present invention, the yield of (-)-epicatechin obtained is about 0.45% of the dried material. The percentage recited herein is % by weight.

The invention further provides a method for the isolation of (-)-epicatechin from a new plant source namely *Dichrostachys cinerea*.

In accordance with this invention, it has been found that (-)-epicatechin is isolated from a new plant source, *Dichrostachys cinerea* in significant yield.

In another invention the process of isolation of (-)-epicatechin is highly economical. *Dichrostachys cinerea* hence is a new plant source for (-)-epicatechin and its presence in this plant in good yields makes this invention more important. The different plant sources from where (-)-epicatechin is isolated are given in Table. 2.

TABLE 2

| Name of the plant | Reference |
|---|---|
| *Acacia catechu* | Indian J.Chem, Sec.B, 1981, 20B(7), 628 |
| *Polygonum multiflorum* | phytochemistry, 1982, 21, 429 |
| *Phyllocladus alpinus* | Phytochemistry, 1985, 24, 1495 |
| *Salix sieboldiana* | phytochemistry, 1985, 24, 2089 |
| *Phyllocladus trichomanoides* | phytochemistry, 1987, 26, 2825 |
| *Brosimopsis actuifolium* | phytochemistry, 1998, 47, 1165 |
| *Dichrostachys cinerea* | Present invention |

Experimental protocol: A process for the isolation of compound (-)-epicatechin. The dried stem bark powder of *Dichrostachys cinerea* (2 Kg) was loaded on a soxhlet apparatus. The powder was first extracted with hexane. The residue from the extraction of hexane was further extracted with chloroform. After the chloroform extraction the residue was taken in a conical flask and soaked in methanol at room temperature. The methanol solution was filtered and concentrated under vacuum (50 g). The methanol extract (50 g) was adsorbed on silica gel (60–120 mesh) and loaded on silica gel (60–120 mesh) column. (5 cms diameter to a height of 100 cms).

The column is subjected to elution with chloroform-methanol gradient. The chloroform-methanol gradient is so selected to obtain specific fraction and thereby the desired compound. In the present case, the fractions eluted at 6% methanol in chloroform are collected separately and concentrated.

The above fractions are subjected to further purification using silica gel column (>200 mesh, 3 cm. dia and 50 cm. length) using chloroform methanol gradient. The eluent at 6% methanol in chloroform gave pure (-)-epicatechin (9.0 g). The spectrochemical data of (-)-epicatechin are given below:

(−)-Epicatechin

1. Molecular formula: $C_{15}H_{14}O_6$
2. $^1$HNMR: [$(CD_3)_2CO$; 200 MHz]:δ 7.04 (1H, d, J 2 Hz, H-2$^1$), 6.86 (1H, d, J 8 Hz, H-5$^1$), 6.78 (1H, dd, J2 and 8 Hz, H-6$^1$), 6.22 (1H, d, J2 Hz, H-8), 6.12
3. (1H, d, J2 Hz, H-6), 4.88 (1H, s, H-2), 4.20 (1H, m, H-3), 2.80 (2H, m, H-4, H-4');
4. $^{13}$C NMR [$(CD_3)_2CO$]: δ 78.13 (C-2), 65.01 (C-3), 28.22 (C-4), 156.57 (C-5), 95.27 (C-6), 156.29 (C-7), 94.22 (C-8), 155.79 (C-9), 98.62 (C-10), 130.69 (C-1$^1$), 118.05 (C-2$^1$), 144.47 (C-3$^1$), 144.54 (C-4$^1$), 114.97(C-5$^1$), 114.90 (C-6$^1$).
5. EIMS: 290 (M$^+$), 272, 152, 139, and 124.
6. IR $\nu_{max}$ (KBr) cm$^{-1}$: 3306
7. $[\alpha]_D^{25}$ −68° (c 0.1, MeOH)

What is claimed is:

1. A process for isolation of (−)-epicatechin from a new plant source *Dichrostachys cinerea*, said process comprising the steps of:

(a) extracting the dried wood powder of *Dichrostachys cinerea* with hexane;
   (b) extracting the residue of step (a) with chloroform;
   (c) extracting the residue of step (b) with methanol solution to obtain a methanolic extract;
   (d) concentrating the methanolic extract of step (c) under vacuum;
   (e) adsorbing the concentrated methanolic extract of step (d) on silica gel and loading on silica gel column;
   (f) eluting the column with chloroform methanol gradient,
   (g) collecting the fraction eluted at 6% methanol in chloroform, and
   (h) concentrating the eluted fraction of step (g) to obtain pure (−)-epicatechin.

2. A process as claimed in claim 1 wherein, the yield of (−)-epicatechin is about 0.45% of the dried material.

* * * * *